United States Patent
Centanni et al.

(10) Patent No.: US 7,087,805 B2
(45) Date of Patent: Aug. 8, 2006

(54) USE OF AN OZONE CONTAINING FLUID TO NEUTRALIZE CHEMICAL AND/OR BIOLOGICAL WARFARE AGENTS

(75) Inventors: Michael A. Centanni, Parma, OH (US); Daniel J. Subach, Beaver Falls, PA (US); Iain F. McVey, Lakewood, OH (US)

(73) Assignee: STERIS Inc., Temecula, CA (US)

( * ) Notice: Subject to any disclaimer, the term of this patent is extended or adjusted under 35 U.S.C. 154(b) by 645 days.

(21) Appl. No.: 10/277,305

(22) Filed: Oct. 22, 2002

(65) Prior Publication Data

US 2004/0077917 A1    Apr. 22, 2004

(51) Int. Cl.
*A62D 3/00*    (2006.01)
(52) U.S. Cl. .............. 588/320; 588/401; 588/405
(58) Field of Classification Search .......... 588/300, 588/313, 317, 318, 400, 401, 405, 410; 422/28, 422/29, 33
See application file for complete search history.

(56) References Cited

U.S. PATENT DOCUMENTS

| | | | |
|---|---|---|---|
| 4,517,159 A | 5/1985 | Karlson | 422/20 |
| 5,430,228 A | 7/1995 | Ciambrone et al. | 588/200 |
| 5,457,269 A | 10/1995 | Schonberg | 588/212 |
| 5,603,750 A | 2/1997 | Sierakowski et al. | 75/743 |
| 5,685,980 A * | 11/1997 | Patapoff et al. | 210/244 |
| 5,689,038 A | 11/1997 | Bartram et al. | 588/200 |
| 5,705,468 A | 1/1998 | Yant et al. | 510/370 |
| 5,763,737 A | 6/1998 | Yang et al. | 588/218 |
| 5,819,673 A | 10/1998 | Heywood et al. | 110/346 |
| 5,897,831 A * | 4/1999 | Jacob et al. | 422/22 |
| 5,945,391 A | 8/1999 | Yant et al. | 510/370 |
| 5,986,160 A | 11/1999 | Bhattacharyya et al. | 588/205 |
| 5,998,691 A | 12/1999 | Abel et al. | 588/200 |
| 6,121,506 A * | 9/2000 | Abel et al. | 588/318 |
| 6,245,957 B1 | 6/2001 | Wagner et al. | 588/200 |
| 6,372,700 B1 | 4/2002 | Zazerra et al. | 510/175 |
| 6,461,487 B1 | 10/2002 | Andrews et al. | 204/262 |
| 6,468,953 B1 | 10/2002 | Hitchems et al. | 510/218 |
| 6,827,766 B1 * | 12/2004 | Carnes et al. | 106/15.05 |

OTHER PUBLICATIONS

Article entitled: "*Rapid Nucleophilic Oxidative Decontamination of Chemical Warfare Agents*." Wagner et al.. Ind. Eng. Chem. Res. (American Chemical Society). vol. 41. No. 8. Mar. 15, 2002. pp. 1925-1928.

U.S. Appl. No. 60/375,851, filed Apr. 24, 2002. McVey et al. entitled: Activated Oxidizing Vapor Treatment System and Method.

U.S. Appl. No. 10/422,474, filed Apr. 24, 2003, McVey et al., entitled: Activated Oxidizing Vapor Treatment System and Method.

* cited by examiner

*Primary Examiner*—Edward M. Johnson
(74) *Attorney, Agent, or Firm*—Kusner & Jaffe; Michael A. Centanni

(57) ABSTRACT

A method and apparatus for neutralizing biological and/or chemical warfare agents using an ozone-containing solution. The ozone-containing solution is produced by combining ozone-containing gas with an ozone vehicle, such as an organic solution. The ozone-vehicle prolongs the shelf life of the ozone to allow for extended periods of storage. A storage container is used to store the ozone-containing solution and facilitate its transportation to an environment contaminated by the biological and/or chemical warfare agents, or near a potential site for biological or chemical attack. The ozone-containing solution is drawn out of the storage container to apply it to a contaminated environment.

12 Claims, 4 Drawing Sheets

USE OF AN OZONE CONTAINING FLUID TO NEUTRALIZE CHEMICAL AND/OR BIOLOGICAL WARFARE AGENTS

FIELD OF THE INVENTION

The present invention relates to neutralization of hazardous contaminants, and more particularly to methods and apparatus for neutralizing chemical and/or biological warfare agents.

BACKGROUND OF THE INVENTION

In recent years, there has been a growing concern over the use of chemical and biological warfare agents by rogue nations and terrorist organizations. One chemical known to be effective in neutralization of most chemical and biological warfare agents is ozone. As is well known to those skilled in the art, ozone is a form of oxygen that has three atoms per molecule rather than two atoms found in oxygen. Ozone ($O_3$) rapidly decomposes into oxygen ($O_2$), as the "extra" oxygen atom splits off the ozone molecule. This "extra" oxygen atom destroys bacteria, and reacts with chemical compounds. Consequently, disinfection and oxidation occur. A common method for producing ozone is to pass air through an electric discharge.

Ozone has been recognized to neutralize most known biological and chemical contaminants, including but not limited to, organosulfur agents, such as mustard gas (H, HD, HS); G-series nerve agents (i.e., organophosphate nerve agents), such as tabun (GA), sarin (GB), soman (GD), and cyclosarin (GF); V-series nerve agents, such as VX, VE, VG, VM and V-gas; vegetative and endospore forming bacteria (e.g., anthrax); fungi; and virus. However, use of ozone to neutralize such contaminants has presented significant logistical problems, since ozone is difficult to store and quickly perishes, due to a short half-life.

The present invention addresses these and other drawbacks of the prior art to provide methods and apparatus for production of ozone, storage of ozone, and application of ozone in environments contaminated by chemical and biological warfare agents.

SUMMARY OF THE INVENTION

In accordance with the present invention, there is provided a method of neuturalizing a biological or chemical warfare agent, comprising the steps of: (a) generating an ozone-containing solution; (b) storing the ozone-containing solution in a storage container near a potential site for chemical or biological attack; (c) releasing the ozone-containing solution from the storage container; and (d) contacting the ozone-containing solution with the biological or chemical warfare agent.

In accordance with another aspect of the present invention, there is provided a method of neutralizing a biological or chemical warfare agent, comprising the steps of: (a) generating an ozone-containing solution; (b) combining the ozone-containing solution with a foam component to produce an ozone-containing foaming composition; (c) storing the ozone-containing foaming composition in a storage container; (d) releasing the ozone-containing foaming composition from the storage container; and (e) contacting the ozone-containing foaming composition with the biological or chemical warfare agent.

In accordance with still another aspect of the present invention, there is provided an apparatus for neutralizing a biological or chemical warfare agent, comprising: (a) solution generating means for generating an ozone-containing solution; (b) storage means for storing said ozone-containing solution; and (c) applicator means for releasing the ozone-containing solution from the storage container and applying the ozone-containing solution to the biological or chemical warfare agent.

In accordance with yet another aspect of the present invention, there is provided a method for sterilizing an instrument, comprising the steps of: (a) mixing an alcohol and ozone to generate an ozone-containing solution; (b) exposing the instrument to the ozone-containing solution, to effect sterilization thereof.

In accordance with yet another aspect of the present invention, there is provided a method of neutralizing a biological and/or chemical warfare agent, comprising the steps of: (a) generating a source of ozone; (b) reacting the ozone with a first chemical to form an activated species; and (c) contacting the activated species with the biological and/or chemical warfare agent to transform the biological and/or chemical into an innocuous chemical.

An advantage of the present invention is the provision of a method and apparatus for the convenient production of ozone.

Another advantage of the present invention is the provision of a method and apparatus for storing ozone.

Another advantage of the present invention is the provision of a method and apparatus for storing ozone that allows for convenient transportation thereof to a contaminated environment.

Another advantage of the present invention is the provision of a method and apparatus for storing ozone that allows for extended shelf-life.

Still another advantage of the present invention is the provision of a method and apparatus for storing ozone that facilitates fast and convenient replenishment of the stored ozone.

Still another advantage of the present invention is the provision of a method and apparatus for applying ozone in a contaminated environment.

Still another advantage of the present invention is the provision of a method and apparatus for monitoring the status of ozone storage containers.

A still further advantage of the present invention is the provision of a logistics system for supplying ozone to a contaminated site to neutralize chemical and/or biological warfare agents.

These and other advantages of the present invention will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Figure 1:
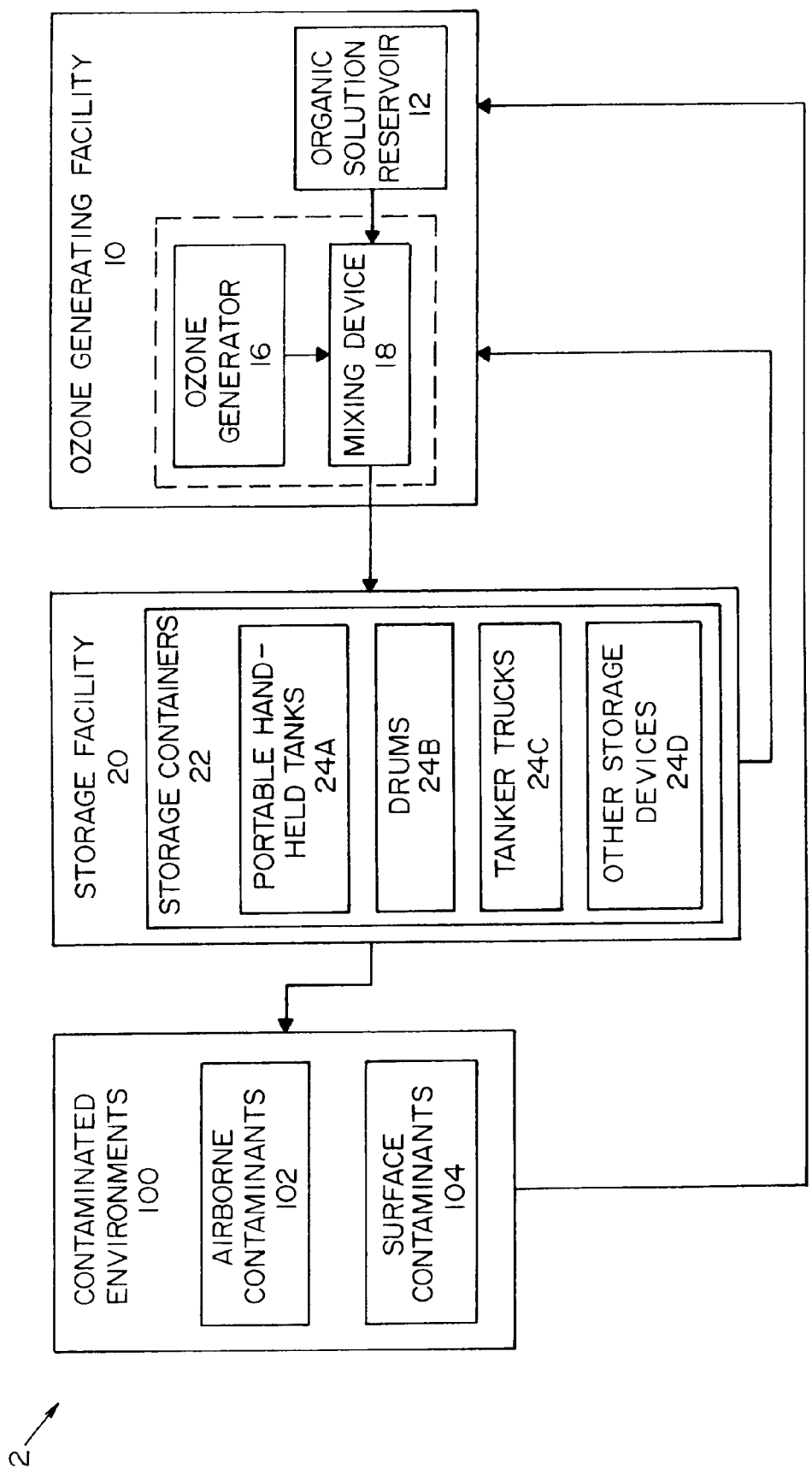
FIG. 1 is a schematic view of a first logistical configuration for the production, storage, and delivery of ozone to a contaminated environment, according to a first embodiment of the present invention.

The invention may take form in various components and arrangements of components, and in various steps and arrangement of steps. The drawings are only for purposes of illustrating a preferred embodiment of the invention only, and not for the purpose of limiting same.

Broadly stated, the present invention is directed to a method and apparatus for the production of ozone, storage of ozone, delivery of ozone to a contaminated environment, and a logistical configuration for carrying out same. Furthermore, the present invention includes apparatus for producing ozone, and storage containers for both storing and applying ozone in a contaminated environment.

Ozone Vehicles (i.e. Fluid Medium)

As indicated above, ozone is an unstable gas. In both air and water, ozone has a short half-life. Consequently, a suitable vehicle is needed to facilitate the storage of high, active concentrations of ozone for extended periods of time. Suitable vehicles include, but are not limited to, water miscible, organic compounds selected from the group consisting of a glycol-containing chemical compound, an alcohol (including but not limited to a tertiary alcohol) and a mixture thereof. The glycol-containing chemical compound may be polyethylene glycol, diethylene glycol, triethylene glycol, tetraethylene glycol, glycol ethers, polypropylene glycol, propylene glycol, or combinations thereof. In a preferred embodiment of the present invention, the ozone vehicle is an alcohol (preferably a tertiary alcohol) or propylene glycol. These vehicles are preferred, since exposure to such vehicles should not pose any serious health risks to humans. Alcohols quickly evaporate, while propylene glycol is a known food additive widely used in the food industry.

The above referenced glycols could be used individually or collectively in combination with other chemicals to increase the stability of ozone in solution, or to improve upon the beneficial properties of ozone. For example, the stability of ozone in solution may be increased by the addition of acetic acid, t-butanol or combinations thereof. Hydrogen peroxide may also be added to enhance the beneficial properties of ozone.

One suitable "ozone vehicle" is comprised of a water miscible, organic compound of a glycol-containing chemical compound, a tertiary alcohol, or a mixture thereof. This organic solution is capable of receiving and containing ozone.

The following steps provide a process for producing an ozone-containing solution comprised of a stable concentration of ozone in the aforementioned organic solution. In this regard, an oxygen-containing gas (e.g., air) or pure oxygen is conveyed to an ozone generator. In a preferred embodiment, an ozone generator generates an ozone-containing gas by exposing the oxygen or oxygen-containing gas to an electric arc, e.g., by electrostatic or corona discharge. The electric arc typically produces ozone gas ranging in concentration from about 0.1 percent (0.1%) ozone gas by volume to about fifteen percent (15%) ozone gas by volume. The ozone-containing gas is conveyed to a compressor where the gas is pressurized, preferably to a pressure of up to about 150 psig. Examples of suitable compressors include a liquid ring or a water piston compressor. The pressurized gas is then conveyed through a conduit to a mixing device. In the mixing device, the ozone is mixed together with an organic solution until an equilibrium pressure, i.e., compared to the pressure of the ozone-containing gas in the conduit, is attained within the mixing device. The pressure in the mixing device is released, followed by removal of the ozone-containing organic solution from the mixing device. All or a portion of the ozone-containing solution may be returned to the mixing device to increase the concentration of ozone therein, by repeating the foregoing process.

In an alternative embodiment, the ozone-containing gas may be introduced simultaneously with the introduction and agitation of the organic solution. In yet another alternative embodiment, the ozone-containing gas may be bubbled through the organic solution while the solution is slowly agitated.

The ozone vehicle described above has been observed to maintain ozone in a solution for over 20 days, at a concentration of nearly 8000 mg/l. Therefore, the ozone vehicle described above has characteristics suitable for use in connection with the neutralization of chemical and/or biological warfare agents, as will be described in further detail below.

A fluorinated solvent composition containing ozone is also known in the prior art. In this regard, ozone is added to a fluorinated solvent immediately prior to use by any conventional technique, such as sparging or gas injection. The ozone is generated using commercially available ozone generators, as described above. The generated ozone is bubbled (i.e. percolated) through the fluorinated solvent. The concentration of the dissolved ozone in the fluorinated solvent is a function of the temperature, pressure and concentration of the gaseous ozone being injected.

With regard to a source of ozone gas, it is well known to those skilled in the art to use an electron beam (e-beam) to irradiate products, such as plastics and foodstuffs. Quantities of ozone are produced as a by-product of the e-beam irradiation process, as the electrons interact with oxygen in the surrounding atmosphere (e.g., air). Ordinarily, this ozone is exhausted by fans as a "waste" product. However, it should be recognized that this ozone by-product may be utilized as a source of ozone in connection with the present invention. In this regard, the ozone produced during an e-beam irradiation process may be extracted and sent to a compressor and combined with an ozone vehicle to produce an ozone-containing solution, as discussed above.

It should also be appreciated that an ozone-containing solution may be combined with a foam component to form an ozone-containing foaming composition. The foam component provides a medium for the ozone-containing solution to reside before and during interaction with contaminants. Furthermore, the foam component provides mechanical agitation of the ozone-containing solution to interact with a contaminant on the surface. As a result, the effectiveness of the ozone may be increased due to the increased interaction of the ozone vehicle with the contaminant. Moreover, the foam component may produce a barrier over a contaminant depending on the thickness of the foam.

A foam component comprises any suitable foam for supporting an ozone-containing solution. By way of example and not limitation, the foam component may take the form of surfactants and stabilizers, such as glycol ethers, fluorochemicals and detergents. The proper amount of foam component combined with the ozone-containing solution is readily determinable by those of ordinary skill in the art.

Storage Containers

Ozone used for decontamination may be dissolved in a liquid solution to form an ozone-containing solution, as discussed above. Containers for storing the ozone-containing solution may range in size from portable handheld tanks and drum canisters (e.g., steel drum), to tanks mounted on trucks or railcars. The selection of an appropriate storage container for ozone-containing solution will depend on a variety of factors, including but not limited to: (a) size of contaminated area, (b) type of environment that is contaminated, (c) size and type of objects within the contaminated area, and (d) travel distance to contaminated area.

Furthermore, the storage containers may be adapted to include means for "charging" the solution stored therein. In this regard, the storage container may be self-contained to include means for generating ozone and means for mixing the ozone with the solution stored therein to produce an ozone-containing solution.

The storage containers are preferably adapted to facilitate the filling and emptying of solution. Accordingly, in a preferred embodiment, the storage containers are adapted to connect with a pump for removing the ozone-containing solution therefrom.

Applicator—Applying Ozone to Contaminated Environments

The ozone-containing solution may be sprayed to form a mist, such as by spray atomization, or can be volatilized to form a gas or other air-mobile fluid. The ozone-containing solution may be removed from the storage container by various means, such as by a pump or by the negative pressure induced by an atomization spray nozzle. It should be appreciated that the ozone-containing solution may also be blended with a solvent, such as water, to improve flow characteristics, if necessary, to make the ozone-containing solution easier to pump and to form a spray or mist.

The selection of sprayer unit (e.g., jet sprayer or aerosol sprayer), and spray pattern is determined based upon the particular application, as well as the formulation and viscosity of the ozone-containing solution. In this regard, a jet sprayer may be more suitable for contaminants located on a surface (e.g., on a military vehicle such as a tank), while an aerosol spray (mist) may be more suitable for airborne contaminants (e.g., the interior of a building).

Decontamination of exposed machinery, and large open areas may be facilitated where the ozone vehicle is supported in a foam component to form a foaming composition. Application of the foaming composition may be by any suitable means for applying a foam onto a contaminated surface. Generally, such application is primarily guided by decreasing the exposure, initial or continuous, of the contaminating agent to personnel. Application of the foaming composition includes, but is not limited to, manual application by a mop, brush, sprayer or other similar manual application, and/or fire-fighting equipment, foam generating equipment or other similar sprayer applications.

Application of the foaming composition includes the steps of mechanical application of the foaming composition onto a contaminated surface, mixing, waiting for the composition to react with the contaminant and rinsing. Although mechanical agitation is provided by the foaming of the decontamination composition, additional mechanical agitation may be supplied, as desired.

Logistical Configurations

It should be understood that the term "charged" refers herein to the state of the ozone-containing solution. In this regard, when the ozone-containing solution contains sufficient ozone content to be effective in neutralizing chemical and/or biological warfare agents, it is considered to be "charged." A "charged" storage container, as used herein, refers to a storage container storing a "charged" ozone-containing solution. "Charging" and "recharging" refer to a process of adding ozone to the ozone vehicle in a sufficient quantity to provide a "charged" ozone-containing solution. A storage container storing ozone-containing solution that requires charging is referred to herein as a "discharged" storage container. "Depleted" or "empty" storage containers refer to storage containers that have little or no ozone-containing solution stored therein.

Referring now to FIG. 1, there is shown a logistical configuration 2 illustrating a first embodiment of the present invention. In this embodiment, the present invention includes an ozone generating facility 10 and a storage facility 20.

Ozone generating facility 10 includes a reservoir 12 suitable for storing an ozone vehicle in the form of an organic solution, an ozone generator 16, and a mixing device 18. Ozone generator 16 generates ozone, in a manner that is well known to those skilled in the art. The ozone is then mixed with the organic solution to dissolve the ozone therein. Together, the ozone and organic solution form an ozone-containing solution that is suitable for decontamination of contaminated environments 100 that may include airborne contaminants 102 and/or surface contaminants 104.

Appropriate storage containers 22 are filled with the ozone-containing solution. Storage containers may take a variety of forms, including but not limited to portable handheld tanks 24A, drums 24B, tanker trucks 24C, and other storage devices 24D (e.g., tanker railcar). These filled storage containers 22 have a limited "useful life." In other words, storage containers 22 will remain useful, i.e. "charged," until the ozone contained within the organic solution dissipates to an ineffectual concentration (i.e., a quantity insufficient to effectively neutralize chemical and/or biological warfare agents).

Charged storage containers 22 may be stored at storage facility 20. It should be appreciated that storage facility 20 may be located in proximity to ozone generating facility 20 or potential sites for biological or chemical attacks, for use in the event such sites become contaminated environments 100, or in locations remote from both. In the event of a chemical or biological attack, charged storage containers 22 are relocated to contaminated environments 100, as needed. A pump or negative pressure induced by an atomization spray nozzle may be used to apply the ozone-containing solution to airborne contaminants 102 and/or surface contaminants 104 of contaminated environments 100.

As discussed above, ozone has a relatively short half life. Therefore, a maintenance regime may be used to maintain an effective schedule for "recharging" storage containers 22. This maintenance regime may be implemented using a scheduler component, including but limited to, a computer-based tracking/scheduling system, a log book, or the like. In the case of a computer-based tracking/scheduling system, a computer database may be used to store identifiers for each storage container along with current information (e.g., date/time of last charging). The maintenance regime may also optionally include a container status component, including but not limited to, date-time tags, timers, gauges, and/or meters. Each container status component is associated with a specific storage container. Furthermore, the container status component is preferably located at or in near proximity to the associated storage container. The scheduler component and container status component provide an indication of when a storage container will require recharging, based upon the half life of the ozone and the charging date/time. A visual and/or audible alarm may be provided to indicate that recharging is needed. For instance, the computer-based tracking/scheduling system may be programmed to send an email to the responsible individual when recharging is needed. Likewise, a meter associated with a storage container 22 could emit an audible alarm when it is determined by the meter that recharging is required.

In accordance with the maintenance regime, discharged storage containers 22 are returned to the ozone generating facility for recharging. In a preferred embodiment, ozone-containing solution stored in the returned storage container 22 is removed therefrom (e.g., by pumping) and transferred to mixing device 18. Ozone generated by ozone generator 16 is mixed with the organic solution removed from storage container 22. The ozone is dissolve in the organic solution to recharge the ozone-containing solution. Thereafter, the returned storage container 22 is refilled with the charged ozone-containing solution, thus providing a "charged" storage container. The charged storage container 22 is then returned to storage facility 20. In an alternative embodiment, the discharged ozone-containing solution removed from the returned storage container 22 is transferred to organic solution reservoir 12. Thereafter, storage container 22 is refilled with charged ozone-containing solution produced by ozone generating facility 10, in the manner described above.

When storage container 22 has been depleted due to application of the ozone-containing solution in a contaminated environment 100, the empty storage container 22 is returned to ozone generating facility 10 for refilling with charged ozone-containing solution, as described above in connection with initial filling of storage containers 22.

Figure 2:
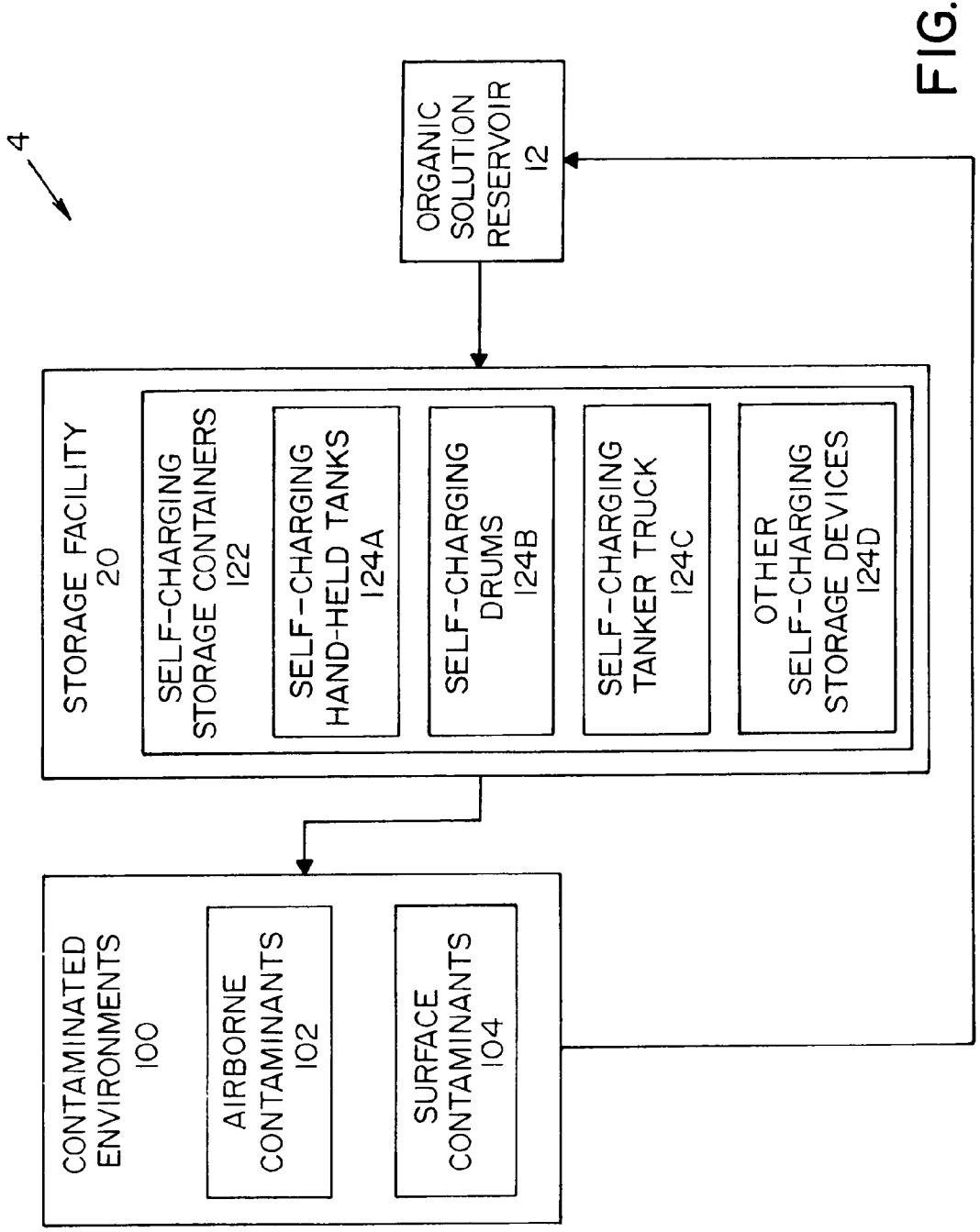
FIG. 2 is a schematic view of a second logistical configuration for the production, storage, and delivery of ozone to a contaminated environment, according to a second embodiment of the present invention.

Referring now to FIG. 2, there is shown a second logistical configuration 4, according to a second embodiment of the present invention. This embodiment of the present invention comprises storage containers 122 that are "self-charging," including, but not limited to self-charging handheld tanks 124A, self-charging drums 124B, self-charging tanker trucks 124C, and other self-charging storage devices 124D. Each storage container 122 incorporates an ozone generator and a mixing device. For instance, the ozone generator may take the form of an electrical transformer, similar to those used in neon signs. The transformer generates a spark that is allowed to arc to a metal grid, wherein the metal grid is a wall of storage container 122. The arc causes the production of ozone and ionic oxygen. The ozone is dissolved into an organic solution using the mixing device, thus producing charged ozone-containing solution. When a self-charging storage container 122 has been depleted due to application of the ozone-containing solution in a contaminated environment 100, the empty self-charging storage container 122 is refilled with organic solution from organic solution reservoir 12. This organic solution is then charged by storage container 122 to produce a charged ozone-containing solution, as described above.

In accordance with a preferred embodiment, self-charging storage containers 122 are recharged in accordance with a maintenance regime, as described above.

Figure 3:
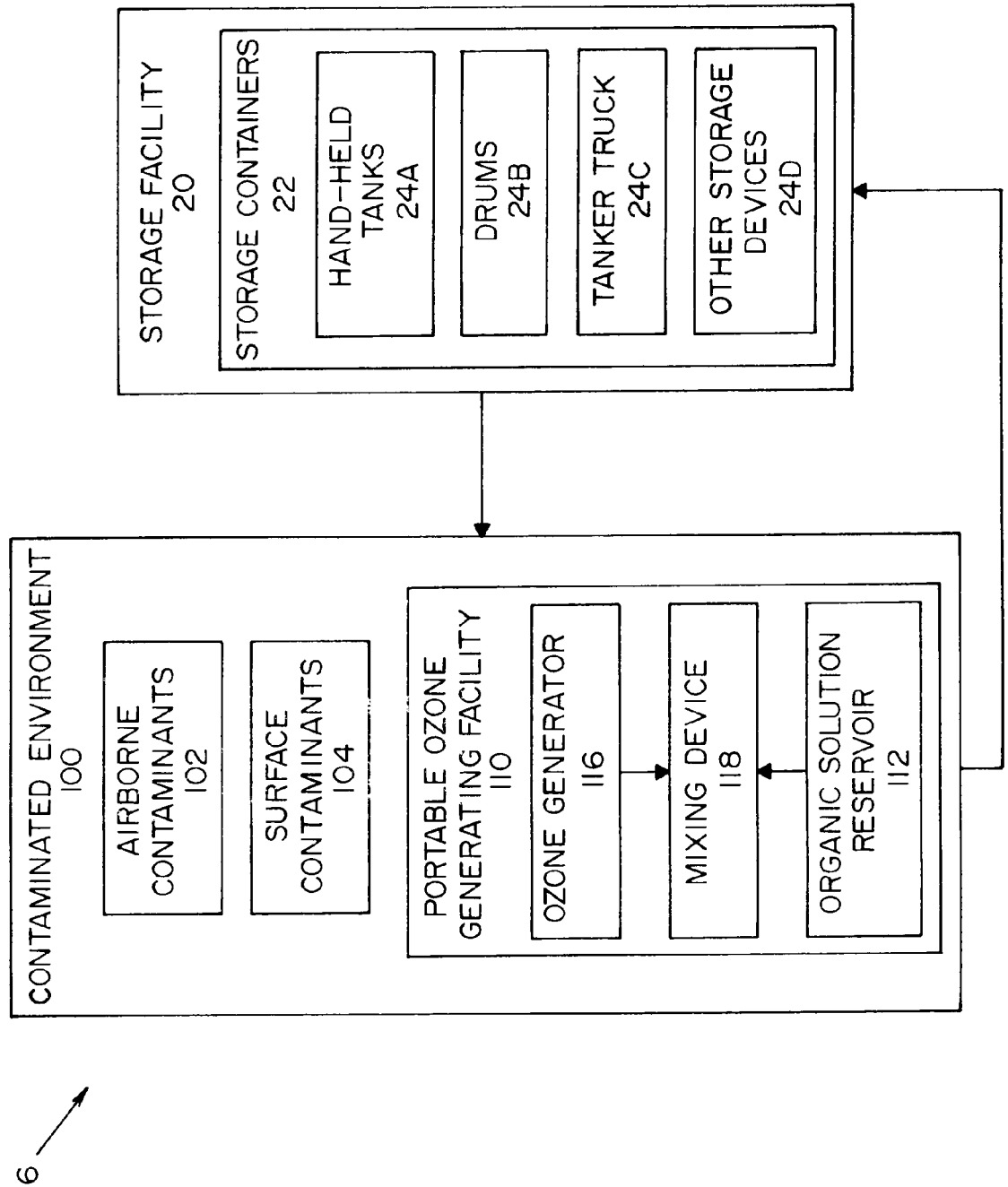
FIG. 3 is a schematic view of a third logistical configuration for the production, storage, and delivery of ozone to a contaminated environment, according to a third embodiment of the present invention.

Referring now to FIG. 3, there is shown a third logistical configuration 6, according to a third embodiment of the present invention. In this embodiment, a portable ozone generating facility 110 is used to fill and charge storage containers 22. Portable ozone generating facility is generally comprised of an ozone generator 116, a mixing device 118 and an organic solution reservoir 112. These components are portable versions of the respective components of the first embodiment of the present invention (FIG. 1). Portable ozone generating facility 110 is preferably located in proximity to contaminated environment 100. This allows unfilled or discharged storage containers 22 to be conveniently transported to contaminated environment 100, where they can be charged as they are used for decontamination.

Figure 4:
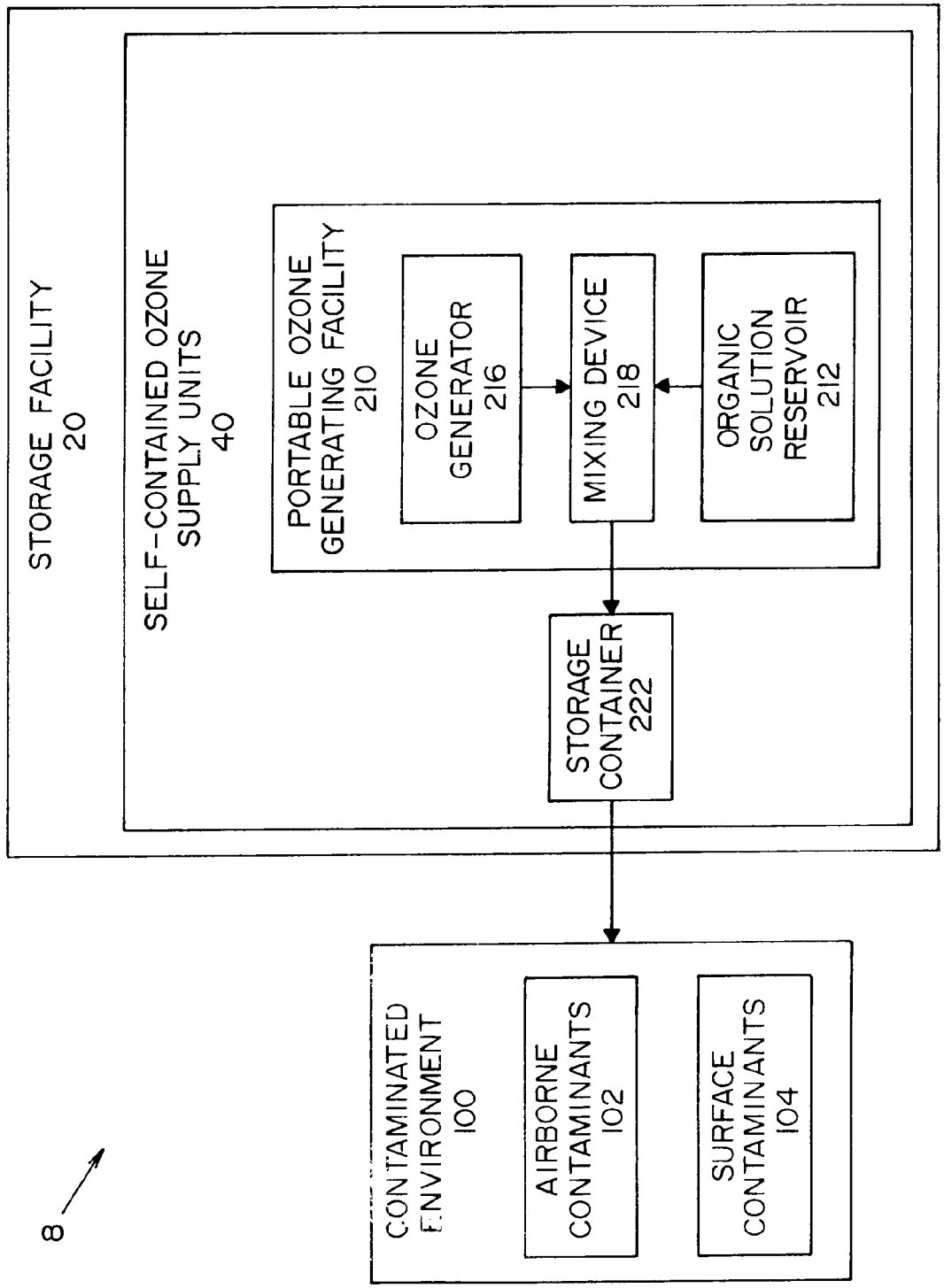
FIG. 4 is a schematic view of a fourth logistical configuration for the production, storage, and delivery of ozone to a contaminated environment, according to a fourth embodiment of the present invention.

Referring now to FIG. 4, there is shown a fourth logistical configuration 8, according to a fourth embodiment of the present invention. In this embodiment, storage facility 20 stores one or more self-contained ozone supply units 40. Supply units 40 are generally comprised of a portable ozone generating facility 210 and storage container 222. Portable ozone generating facility 210 includes an organic solution reservoir 212, an ozone generator 216, and a mixing device 218. In a preferred embodiment, self-contained ozone supply units 40 take the form of a tanker truck or railcar that can be conveniently transported to contaminated environment 100. In this embodiment, storage container 222 preferably takes the form of a large tank, or one or more small tanks.

It should be understood that the present invention is not limited to ozone-containing solutions, but may also be extended to other oxidizing agents, including but not limited to, fluorinated compounds holding oxidizing agents, such as chlorine dioxide.

It should be recognized that the present invention also finds utility in the field of sterilization. For instance, an ozone-containing solution comprised of a tertiary alcohol and ozone, may be suitably used as a sterilant for sterilizing devices, such as medical instruments, and more preferably, medical instruments made of metal (e.g., stainless steel). In an exemplary embodiment, the medical instruments are first washed to remove soil (e.g., blood, tissue, and the like). Thereafter, the medical instruments are placed in a container. The ozone-containing solution comprised of tertiary alcohol and ozone is then pumped into the container to effect sterilization of the medical instruments. After sufficient exposure to the ozone-containing solution, the medical instruments are removed from the container.

In an alternative embodiment of the present invention ozone is "directly" utilized. In this regard, a supply of ozone is produced by pumping oxygen into an ozone-generating device, or is produced as a by-product of an e-beam irradiation process. The supply of ozone is then pumped directly to a contaminated environment, for contact with airborne and/or surface contaminants. In this alternative embodiment, an ozone vehicle is unnecessary.

It is also contemplated that the ozone of the present invention may be exposed to a chemical that reacts therewith, to form an "activated species." The activated species may then be released in a contaminated environment to react with and pacify airborne and/or surface contaminants of biological and/or chemical agent(s), to transform the biological and/or chemical agent(s) into an innocuous chemical. For instance, an oxygen atom from ozone reacts with sodium azide to form an activated species that can be reacted with GB (sarin) or GD (soman), to replace the flouride with ammine. Furthermore, an oxygen atom from ozone reacts with alkylazoalkoxy to form an activated species that can be reacted with GB or GD, to replace the flouride with hydroxyl. As another example, an oxygen atom from ozone reacts with $H_2O_2$ to form an activated species that can be reacted with VX to form a sulfoxide from a sulfide linkage.

In yet another example, an oxygen atom from ozone reacts with $H_2O_2$ and HOH/HX (where X is a halogen), to form an activated species that can be reacted with GA (tabun). The GA breaks down into an alcohol and carboxylic acid or halide intermediate.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method of neutralizing a biological or chemical warfare agent, comprising:
   generating an ozone-containing gas;
   mixing the ozone-containing gas with an ozone vehicle to produce an ozone-containing solution, wherein said ozone vehicle facilitates stability of the ozone-containing gas, said ozone vehicle selected from the group consisting of: a glycol-containing chemical compound, an alcohol, and a mixture thereof;
   storing said ozone-containing solution in a self-charging storage container near a potential site for chemical or biological attack;
   recharging said ozone-containing solution within said self-charging storage container in accordance with a predetermined criteria to increase ozone content of the ozone-containing solution stored in said self-charging storage container, wherein said predetermined criteria includes at least one of the following: elapsed time and ozone content of the ozone-containing solution within said self-charging storage container, wherein said step of recharging said ozone-containing solution within said self-charging storage container includes the steps of:
      generating ozone inside said self-charging storage container using an ozone generator, wherein generation of the ozone is initiated by the self-charging storage container; and
      mixing the generated ozone with said ozone-containing solution inside said self-charging storage container to recharge said ozone-containing solution, wherein mixing of the generated ozone with said ozone-containing solution is initiated by the self-charging storage container;
   releasing the ozone-containing solution from the self-charging storage container; and
   contacting the ozone-containing solution with the biological or chemical warfare agent released from the self-charging storage container.

2. A method as defined in claim 1, wherein said ozone-containing gas is mixed with said ozone vehicle under pressure.

3. A method as defined in claim 1, wherein said ozone-containing gas is bubbled through the ozone vehicle while said ozone vehicle is agitated by a mixing device.

4. A method as defined in claim 1, wherein said ozone-containing gas is generated by exposing oxygen to an e-beam.

5. A method as defined in claim 1, wherein said ozone-containing solution further includes water.

6. A method as defined in claim 1, wherein said glycol-containing chemical compound is selected from the group consisting of: polyethylene glycol, diethylene glycol, triethylene glycol, tetraethylene glycol, glycol ethers, polypropylene glycol, propylene glycol, and combinations thereof.

7. A method as defined in claim 1, wherein said alcohol is a tertiary alcohol.

8. A method as defined in claim 1, wherein said glycol-containing chemical compound is propylene glycol.

9. A method as defined in claim 1, wherein said ozone-containing solution is atomized as it is released from the self-charging storage container.

10. A method as defined in claim 1, wherein said ozone-containing solution further includes additives selected from the group consisting of: hydrogen peroxide, acetic acid, t-butanol and combinations thereof.

11. A method as defined in claim 1, wherein said self-charging storage container is selected from the group consisting of: a handheld portable container, a drum container, a tanker truck, and a tanker railcar.

12. A method of neutralizing a biological or chemical warfare agent, comprising:
   mixing the ozone-containing gas with an ozone vehicle to produce an ozone-containing solution, wherein said ozone vehicle facilitates stability of the ozone-containing gas, said ozone vehicle selected from the group consisting of: a glycol-containing chemical compound, an alcohol, and a mixture thereof;
   combining the ozone-containing solution with a foam component to produce an ozone-containing foaming composition;
   storing the ozone-containing foaming composition in a self-charging storage container;
   recharging said ozone-containing foaming composition within said self-charging storage container in accordance with a predetermined criteria to increase ozone content of the ozone-containing foaming composition stored in said self-charging storage container, wherein said predetermined criteria includes at least one of the following: elapsed time and ozone content of the ozone-containing foaming composition within said self-charging storage container, wherein said step of recharging said ozone-containing foaming composition within said self-charging storage container includes the steps of:
      generating ozone inside said self-charging storage container using an ozone generator, wherein generation of the ozone is initiated by the self-charging storage container; and
      mixing the generated ozone with said ozone-containing foaming composition inside said self-charging storage container to recharge said ozone-containing foaming composition, wherein mixing of the generated ozone with said ozone-containing solution is initiated by the self-charging storage container;
   releasing the ozone-containing foaming composition from the self-charging storage container; and
   contacting the ozone-containing foaming composition with the biological or chemical warfare agent released from the self-charging storage container.

* * * * *